United States Patent
Chapkin et al.

(12) 
(10) Patent No.: US 6,258,541 B1
(45) Date of Patent: Jul. 10, 2001

(54) NONINVASIVE DETECTION OF COLONIC BIOMARKERS USING FECAL MESSENGER RNA

(75) Inventors: Robert S. Chapkin; Laurie A. Davidson; Joanne R. Lupton, all of College Station, TX (US)

(73) Assignee: Texas A&M University, College Station, TX (US)

(*) Notice: Subject to any disclaimer, the term of this patent is extended or adjusted under 35 U.S.C. 154(b) by 0 days.

(21) Appl. No.: 09/381,086
(22) PCT Filed: Apr. 3, 1998
(86) PCT No.: PCT/US98/06698
  § 371 Date: Sep. 14, 1999
  § 102(e) Date: Sep. 14, 1999
(87) PCT Pub. No.: WO98/45480
  PCT Pub. Date: Oct. 15, 1998

Related U.S. Application Data (60) Provisional application No. 60/043,048, filed on Apr. 4, 1997.

(51) Int. Cl.[7] ............................... C12Q 1/68; C12P 19/34
(52) U.S. Cl. ............................ 435/6; 435/91.1; 435/91.2
(58) Field of Search ............................... 435/6, 91.1, 91.2

(56) References Cited

PUBLICATIONS

Ambion Inc. from Ambion.com website: description of poly(A) pure kits, and protocol, 1995.*
Barbee et al, Gene, vol. 132, pp 305–306, 1993.*
Greenham et al., Human Genetics, vol. 103, pp 483–487, 1998.*
Jiang et al.: "Rapid Competitive PCR Determination of Relative Gene Expression in Limiting Tissue Samples" Clin. Chemistry, vol. 42, No. 2, 1996, pp. 227–331, XP002075087.
Davidson et al.: "Noninvasive Detection of Putative Biomarkers for Colon Cancer Using Fecal Messenger RNA" Canc. Epidem. Biomarkers and Prevention, vol. 4, 1995, pp. 643–647, XP002075091.
Jiang et al.: "Dietary Fish Oil Blocks Carcinogen–Induced Down–Regulation of Colonic Protein Kinase C Isozymes" Carcinogenesis, vol. 18, No. 2, Feb. 1997, pp. 351–357, XP002075088.
Hardie and Hanks: "The Protein Kinase Factsbook; vol. 1: Protein–Serin Kinases" 1995, Academic, London, GB XP002075310, see pp. 80–88.
Blobe et al.: "Protein Kinase C Isozymes: Regulation and Function" Cancer Surveys, vol. 27, 1996, pp. 213–248, XP002075089.
Davidson et al.: "Protein Kinase C Isoforms in Human and Rat Colonic Mucosa" Arch. of Biochem. and Biophys., vol. 312, No. 2, 1994, pp. 547–553, XP002075090.
Davidson et al.: "Non–Invasive Detection of Fecal Protein Kinase C Beta II and Zeta Messenger RNA: Putative Biomarkers for Colon Cancer" Carcinogenesis, vol. 19, No. 2, 1998, pp. 253–257, XP002075092.

* cited by examiner

*Primary Examiner*—Lisa B. Arthur
*Assistant Examiner*—Jehanne Souaya
(74) *Attorney, Agent, or Firm*—Fulbright & Jaworski (57) ABSTRACT

A noninvasive method utilizing feces, containing sloughed colonocytes, as a sensitive technique for detecting diagnostic colonic biomarkers as well as a method for isolating poly A +RNA from feces. The method allows the isolation and quantitation of specific eukarotic mRNAs as candidate biomarkers for colon cancer isolated from feces.

13 Claims, 8 Drawing Sheets

NONINVASIVE DETECTION OF COLONIC BIOMARKERS USING FECAL MESSENGER RNA

CROSS-REFERENCE TO RELATED APPLICATIONS

This application was filed under 37 CFR 371 from PCT Application No. PCT/US98/06698 filed Apr. 3, 1998, which claims priority of U.S. Provisional Patent Application Ser. No. 60/043,048, filed Apr. 4, 1997, both being incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to methods for the noninvasive detection of colonic biomarkers using fecal messenger RNA (mRNA). More particularly, the present invention relates to methods for the isolation of poly A+ RNA from feces, and includes the subsequent detection of, and quantitation of, particular mRNAs that correlate with a patient's diagnosis and/or prognosis of colon cancer thereby providing methods for noninvasively diagnosing and/or prognosticating colon cancer in a patient. One embodiment of the present invention relates to the detection of, and quantitation of, mRNA from sloughed colon cells in feces encoding particular isozymes of protein kinase C (PKC) whose levels are correlative with and predictive of colon cancer in a patient. Methods including semi-quantitative RT-PCR and biochip microarray technology may be made to assay and evaluate the fecal poly A+RNA.

2. General Background

Since colon cancer is the second most common cause of U.S. cancer deaths and since early detection can result in a high cure rate, an accurate screening method for colon cancer is imperative. Current detection methods have many drawbacks. For example, fecal occult blood screening can produce false positive results due to meat consumption, iron supplement intake and other common behaviors. The other routine screening technique, sigmoidoscopy, is an invasive expensive procedure which has inherent risks of perforation, reaction to sedative, or bleeding. In addition, the efficacy of sigmoidoscopy screening remains unproven (Levin, 1996). Because of these limitations, colon cancer cure rates have not improved in the past 30 year (Silverberg, 1988, WFR/AICR, 1997). Therefore, an accurate technique to detect early changes associated with the tumorigenic process is imperative in order to decrease the mortality from colon cancer.

Screening of colorectal cancer is recommended for all persons aged 50 and older with annual fecal occult blood testing or sigmoidoscopy, or both (Levin, 1996). However, each of these tests has limitations related to sensitivity and specificity (Levin, 1996). The presence of colorectal and pancreatic tumors has been detected in the stool and colonic effluent of patients by noninvasive methods based on the molecular pathogenesis of the disease (Sidransky, 1992: Tobi, 1994; Caldas, 1994). These protocols utilize DNA extraction procedures and the detection of oncogene mutations using PCR. The major disadvantage of this methodology is that it will not detect alterations in gene expression. Our methodology can quantitate the expression of any relevant gene by isolating and amplifying mRNA derived from fecal material containing sloughed colonocytes.

A sensitive molecular technique for the detection of colon cancer is important since early diagnosis can substantially reduce mortality (Levin, 1996). Our method is noninvasive, highly sensitive and specific. Our protocol is unique because it will determine colonic expression of any gene (e.g., tumor suppressor gene, oncogene), and provides early sensitive prognostic information and greatly enhances current methods of dietary and pharmacologic risk assessment.

SUMMARY OF THE PRESENT INVENTION

The present invention relates to a novel non-invasive technology to detect changes in colonocyte gene expression associated with early stages of colon tumorigenesis. This invention also covers the first known methods to isolate poly A+ RNA from feces. This methodology has the advantage of utilizing a fecal sample, which contains sloughed colon cells. Therefore, it does not require anesthesia or cause any discomfort to the patient. In addition, the invention utilizes a novel mRNA isolation process that results in an unexpectedly high yield and stability of isolated fecal mRNA, and utilizes an exquisitely sensitive technique, rapid competitive polymerase chain reaction (Jiang, 1996), developed by the inventors, to detect and quantify mRNA markers of the tumorigenic process. Thousands of gene markers for the tumorigenic process are assayable in the practice of the present invention. These markers include, but are not limited to, PKC isozymes such as, for example, PKC βII (PKC beta II) and PKC ζ (PKC zeta), where, for example, levels of these particular isozymes in feces are correlative of and predictive of the presence of, and development of colon cancer in a rat colon cancer model (Davidson, 1998). We have also successfully isolated poly A+ RNA from rectal vault eluate isolated at the initiation of colonoscopy. Yields from fecal eluate are generally in the range of 0.3–1.5 µg poly A+ RNA isolated per subject.

The pathogenesis of colon cancer is a multi-step process, in which tumor suppressor genes, oncogenes and other molecules involved in signal transduction are affected (Fearon, 1997). It is now clear the signals mediated via select isozymes of protein kinase C (PKC) are involved in colonic tumor development (Sakanoue et al., 1991; Kopp et al. 1991; Baum et al., 1990). PKCs are a family of serine-threonine kinases thought to regulate colonic cell proliferation, differentiation and programmed cell death. PKCs can be divided into three different sub-categories based on the cofactors needed for activation: classical PKCs (α, βI, βII and γ) require diacylglycerol (DAG) and $Ca^{2+}$ for activation; novel PKCs (δ, θ, η and ε) are $Ca^{2+}$ independent, but activated by DAG; and atypical PKCs (λ, ι and ζ) are $Ca^{2+}$ and DAG independent. Although these isozymes are enzymatically similar, in vivo, they have different expression patterns depending on tissue and cell type (Blobe et al., 1996).

PKC βII protein is generally found in very low levels in normal rat colonic mucosa (Davidson et al., 1994). However, βII protein levels increase in colonic tumors as compared with normal colonic mucosa (Craven et al., 1992; Wali et al., 1995). In contrast, PKC ζ mRNA levels are significantly lower in human colorectal tumors than in normal colonic mucosa (Kuranami et al., 1995). PKC ζ protein levels also are significantly lower in preneoplastic colonic epithelium from rats injected with azoxymethane (AOM) as compared with saline-injected control rats (Wali et al., 1995; Roy et al., 1995; Jiang et al., 1997). Therefore PKC βII and ζ may serve as biomarkers to monitor the development of colon cancer.

In summary, no one has reported the isolation of intact poly A+ RNA from fecal material or rectal eluates obtained at colonoscopy. Utilization of this noninvasive procedure combined with either RT-PCR analyses or genechip microarrays is novel.

BRIEF DESCRIPTION OF THE DRAWINGS

For a further understanding of the nature and objects of the present invention, reference should be had to the following detailed description taken in conjunction with the accompanying drawings, in which like parts are given like reference numerals and wherein:

FIG. 4 shows expression of PKC βII in fecal poly A+ RNA or colonic mucosal RNA. Rats were injected with azoxymethane (AOM) or saline twice. Feces were collected 36 weeks after the second injection and poly A+ RNA was isolated. Colonic mucosa was scraped and total RNA was isolated. Quantitative RC-PCR was performed using primers specific for PKC βII. PCR products were separated on 4% agarose gels, stained with ethidium bromide, photographed and scanned on a densitometer to quantitate. Y-axis represents band intensities (OD×mm$^2$). (A) Expression of PKC βII in fecal poly A+ RNA from rats with or without tumors (mean±SEM; P=0.026; n=12–29). (B) Expression of PKC βII in colonic mucosal RNA from rats injected with AOM or saline (mean±SEM; P=0.036; n=16–20). "BI" is "band intensity", "T" is "tumor", "NT" is "no tumor", "I" is "injection", and "S" is "saline".

DETAILED DESCRIPTION OF THE PREFERRED EMBODIMENT

The development of noninvasive techniques, as shown in this invention, provides early sensitive prognostic information and will greatly enhance the current methods of dietary, pharmacologic, and cancer risk assessment. The present invention describes a noninvasive method utilizing feces containing sloughed colonocytes as a sensitive technique for detecting diagnostic biomarkers in the colon. By incorporating a novel method of isolating fecal mRNA and by utilizing the exquisite sensitivity of quantitative rapid competitive reverse transcriptase polymerase chain reaction (RC-PCR), the method is capable of isolating and quantitating specific messenger RNAs (mRNAs) as candidate biomarkers in feces. The RNA can also be assayed and evaluated using nucleic acid "biochip"/"microarray" technology as described below and as understood in the art. This technology allows for large-scale high-throughput monitoring of gene expression patterns of up to 40,000 genes (Lipshutz, 1999). Further, the present invention has recognized a correlation between levels of particular biomarkers and the presence of and development of colon cancer.

For example, but not in a limiting sense, the present invention recognizes that PKC βII expression in fecal poly A+ RNA is positively correlated with tumor incidence and the expression of PKC ζ is negatively correlated with tumor incidence (Davidson, 1998).

The method of the present invention involves a novel technique of isolating mRNA from feces that results in, inter alia, substantial improvement in yield, and stability of isolated poly A+ RNA from exfoliated colonocytes in feces, in a substantially reduced amount of time compared with the only other known techniques in the art (the technique of Davidson, 1995).

Approximately one-sixth to one-third of normal adult colonic epithelial cells are shed daily (Potten, 1979). Isolation of colonocytes from feces has been reported by another group (Albaugh, 1992). This method is very time consuming and results in an extremely low yield such that useful diagnostic tests on the isolated cells are limited and very labor intensive. We therefore designed a technique to directly isolate poly A+ RNA from feces containing exfoliated colonocytes. The poly A+ RNA isolated can be used to probe for early markers for colon cancer or other colorectal diseases.

Specifically, we have redesigned the protocol of the prior art (for example, Davidson, 1995) to significantly simplify and enhance the process, resulting in a greatly enhanced yield. In addition, we have combined the improved isolation protocol with an extremely sensitive detection technique, called rapid competitive polymerase chain reaction (RC-PCR), a technology developed in our laboratory.

The original method (Davidson, 1995) involved the isolation of total RNA from feces followed by poly A+ RNA isolation, which could subsequently be utilized for assessment of colon cancer biomarkers. This older methodology resulted in a relatively low yield of poly A+RNA, thereby limiting the diagnostic tests which could be performed. The modifications, detailed below, result in approximately 10-fold increase in poly A+ RNA yield, allowing for extensive screening of various colon cancer biomarkers. In addition, the method is straight-forward and could be performed by a trained technician. Several samples (up to 12 or more) can be processed at once.

The refined RNA isolation technology of the present invention has been validated using the rat chemical carcinogen model. Specifically, we have demonstrated that protein kinase C (PKC) βII and PKC ζ G in exfoliated colonocytes may serve as noninvasive markers for development of colon tumors (Davidson, 1998).

The improved method is an improvement on the basic method set forth by Laurie A. Davidson, Yi-Hai Jiang, Joanne R. Lupton, and Robert S. Chapkin in Noninvasive Detection of Putative Biomarkers for Colon Cancer Using Fecal Messenger RNA, published in *Cancer Epidemiology, Biomarkers & Prevention*, Vol. 4, 643–647, Sept., 1995— this paper is hereby incorporated by reference in its entirety. Instant improvements include, for example, poly A+ RNA is directly isolated from feces using oligo dT cellulose based methodology. The previous published report (Davidson, 1995) involved total RNA isolation from feces followed by poly A+ isolation from the total RNA preparation. The improved method shortens the poly A+ RNA isolation to 5 h (from 2 d with the previous methodology) and significantly increases yield by 5–10 fold.

In still another feature of the present invention, and an improvement over the prior art, the present invention is suitable for the detection, and quantitation of specific biomarkers whose expression in colon cells and thus, in poly A+ RNA isolated from feces, correlates with and is predictive of states of colon cancer in a patient.

For example, the present invention shows that PKC βII and PKC ζ are suitable as biomarkers for monitoring the development of colon cancer. The modulation of these putative biomarkers—affected by the presence or absence of colon tumors is shown herein. Weanling rats were injected with saline (control) or carcinogen (azoxymethane). Fresh fecal samples (n=6 per diet) were collected 36 weeks post injection, poly A+ RNA was isolated and quantitative RC-PCR performed using primers to PKC βII and ζ. PKC isozyme expression was altered by the presence of tumors (P<0.05), with tumor bearing animals having a 3-fold higher βII expression and 6-fold lower ζ expression in exfoliated colonocytes than non-tumor bearing animals. We propose that expression of PKC βII and ζ in exfoliated colonocytes may serve as a noninvasive marker for development of colon tumors.

Also novel is the use of the rapid competitive PCR method (as first disclosed in Jiang, 1996) to sensitively quantify biomarker expression in fecal poly A+ RNA. This method is described in detail in *Rapid competitive PCR determination of relative gene expression in limiting tissue samples*, Yi-Hai Jiang, Laurie A. Davidson, Joanne R. Lupton, and Robert S. Chapkin, *Clinical Chemistry*, 42:2, 227–231 (1996), which is hereby incorporated by reference in its entirety. This method is ideal for limited RNA samples, since it requires only a single PCR reaction in order to determine relative gene expression. In contrast, the more traditional mimic reverse transcriptase (RT)-PCR technique requires a series of 5 to 7 PCR reactions in order to quantitate gene expression.

For example and for illustrative purposes only, at least the following features of the present invention are novel over the prior art: (1) Direct isolation of poly A+ RNA from feces or rectal eluates; (2) Ten-fold increase in poly A+ yield with decrease in processing time by more than 50%; (3) Identification of protein kinase C (PKC) βII as a marker for colon cancer; (5) Use of the novel relative competitive RC-PCR method to detect and quantify markers of colon cancer in feces containing exfoliated colon cells; and (6) Validation of fecal homogenate stability after processing and storage prior to poly A+ isolation.

The methods of the present invention can be utilized to detect predictive risk markers for colon cancer including, but not limited to, biomarkers such as:
Acyl CoA Binding Protein (ACBP) expression
Arginase expression
bax expression
bcl-2 expression
Bcl-XL expression
Bcl-Xs expression
c-myc expression
Carcinoembryonic Antigen (CEA) and Nonspecific Cross-reacting Antigen (NCA) expression
CD44 Glycoprotein expression
Cyclin-dependent kinase inhibitors (p27, p16ink4) expression
Cyclin-dependent kinase cdk2/cdc2, cyclin D1, and cdk4 expression
Cyclooxygenase I and II
Decay Activating Factor expression
E-Cadherin cell adhesion molecule expression
Epidermal Growth Factor Receptor (EGFR) expression
Fatty Acid Synthase expression
Fecal alpha-1 Antitrypsin expression
GDP-L-fucose:beta-D-galactoside-alpha-2-L-fucosyltranferase expression
Gluthathione S-Transferase expression
Histone H3 expression
Interleukin 1 and 2 expression
Liver and Intestinal Fatty Acid Binding Protein expression
hTERT expression
Mitogen-activated protein kinase (MAP kinase) expression
MAP kinase phosphatase-1 expression
NO synthase, inducible expression
Ornithine Decarboxylase expression
p21 waf 1/cip 1 expression
P-glycoprotein, the mdr gene product expression
Plasminogen Activator expression
Proliferating cell nuclear antigen (PCNA) expression
Prostaglandin Synthase Type II (COX II) expression
Protein Kinase A, Type I and II Isozyme expression
Protein Kinase C α, βII, δ, ε, λ, ι, μ, ζ expression
Ras oncogene expression
Ras oncogene mutations
Stearoyl-CoA desaturase expression
Sterol Carrier Protein-2 (SCP-2) expression
Telomerase expression
Transforming Growth Factor-beta I and II expression
Transforming Growth Factor-beta type II Receptor expression and mutations
Tumor Necrosis Factor Alpha expression
Tumor suppressor gene APC mutations
Tumor suppressor gene p53 mutations and expression
Tumor suppressor gene retinoblastoma (Rb) protein expression
Villin expression 1,25-dihydroxyvitamin D3 Receptor expression, and 13-hydroxyoctadecadienoic acid (13-HODE) dehydrogenase expression.

The present invention is suitable for noninvasive detection of any diagnostic gene or panel of genes including PKC isozymes as predictive risk markers for human colon cancer. We have already validated the use of select PKC isozymes as predictive risk markers using the rat experimental colon cancer model (Davidson, 1998). In addition, we have isolated human poly A+ RNA from feces and rectal eluates and detected the presence of PKC isozymes.

Additionally, the present invention, using, for example the rat colon cancer model, relates to the determination of the temporal effects of carcinogen on select PKC isozyme fecal mRNAs.

The development of noninvasive techniques, as shown in this invention, provide early sensitive prognostic information and greatly enhance current methods of dietary and pharmacologic risk assessment. The method reported herein is novel since it is the first to report that poly A+ RNA from exfoliated colonocytes can be isolated directly from feces or rectal eluates and can be used to probe for markers of colon cancer. Several markers have also been identified that are present in fecal poly A+ RNA that predict for colon cancer.

EXPERIMENT 1

Utilization of Isolated Fecal Poly A+ RNA to Detect Colon Cancer Markers

Further details related to this method may be found in the article by Laurie A. Davidson, Christin M. Aymond, Yi-Hai Jiang, Nancy D. Turner, Joanne R. Lupton and Robert S. Chapkin, entitled "Non-invasive detection of fecal protein kinase C βII and ζ messenger RNA: putative biomarkers for colon cancer", published in *Carcinogenesis*, vol. 19, no. 2, pp. 253–257, 1998, which is hereby incorporated by reference in its entirety.

Experimental Methods

Isolation of poly A+ RNA from feces:
1. Collect 0.3–2.0 g of rat or human feces. Within 30 min of defecation, add 10 volumes of Lysis Solution (available from Poly A+ Pure Kit, Ambion, Austin, Tex.) ("Ambion Kit"). Homogenize feces with a pestle. This homogenate can be stored at −80° C. for several months before further processing.
2. Transfer homogenate to sterile 50 ml conical Falcon tube and measure the volume. Add 2 vol Dilution Buffer (Ambion Kit). Mix by inversion for 10 sec. Centrifuge at 4,000×g, 15 min, 4° C. Transfer supernatant to a new sterile 50 ml Falcon tube.
3. Add oligo dT cellulose (Ambion Kit), an amount equal to 10% of the starting fecal weight. Mix by inversion to resuspend the oligo dT resin.
4. Rock the tube on a horizontal shaker at 100–150 rpm at room temperature for 1 hr.
5. Pellet the oligo dT resin by centrifuging at 4,000×g, 3 min, 4° C. Remove and discard the supernatant.
6. Resuspend the resin with 6–10 ml Binding Buffer (Ambion Kit) and mix well. Pellet resin as described in step 5 and discard. Repeat this two more times.
7. Resuspend resin with 6–10 ml Wash Buffer (Ambion Kit) and mix well. Centrifuge as described in step 5 and discard supernatant. Repeat this wash two more times.
8. Resuspend the resin in 1–2 ml wash buffer and transfer to a spin column in a 1.5 ml microfuge tube (Ambion Kit). Centrifuge at 5,000×g, 10 sec, room temperature to remove the supernatant. Place spin column into a new microfuge tube.
9. Add 300 μl Elution Buffer (Ambion Kit) which has been pre-warmed to 65° C. Immediately centrifuge at 5,000×g, room temperature, 30 sec and save the eluate. Add another 300 μl pre-warmed Elution Buffer and centrifuge at 5,000×g, room temperature, 30 sec. Combine eluate with previous eluate. Discard the spin column.
10. Precipitate the poly A+ RNA by adding 60 μl 5M ammonium acetate, 10 μg glycogen and 2.5 vol 100% ethanol. Place at −80° C. for 1 h. Recover poly A+ RNA by centrifugation at 12,000×g, 20 min, 4° C. Remove and discard supernatant, add 0.5 ml chilled 80% ethanol to the tube, invert tube gently. Resuspend the poly A+ pellet in 60–200 μl water/0.1 mM EDTA. Vortex gently to resuspend.

This purified A+ RNA is used for colon cancer biomarker studies such as those detailed below:

Results

Figure 4A:
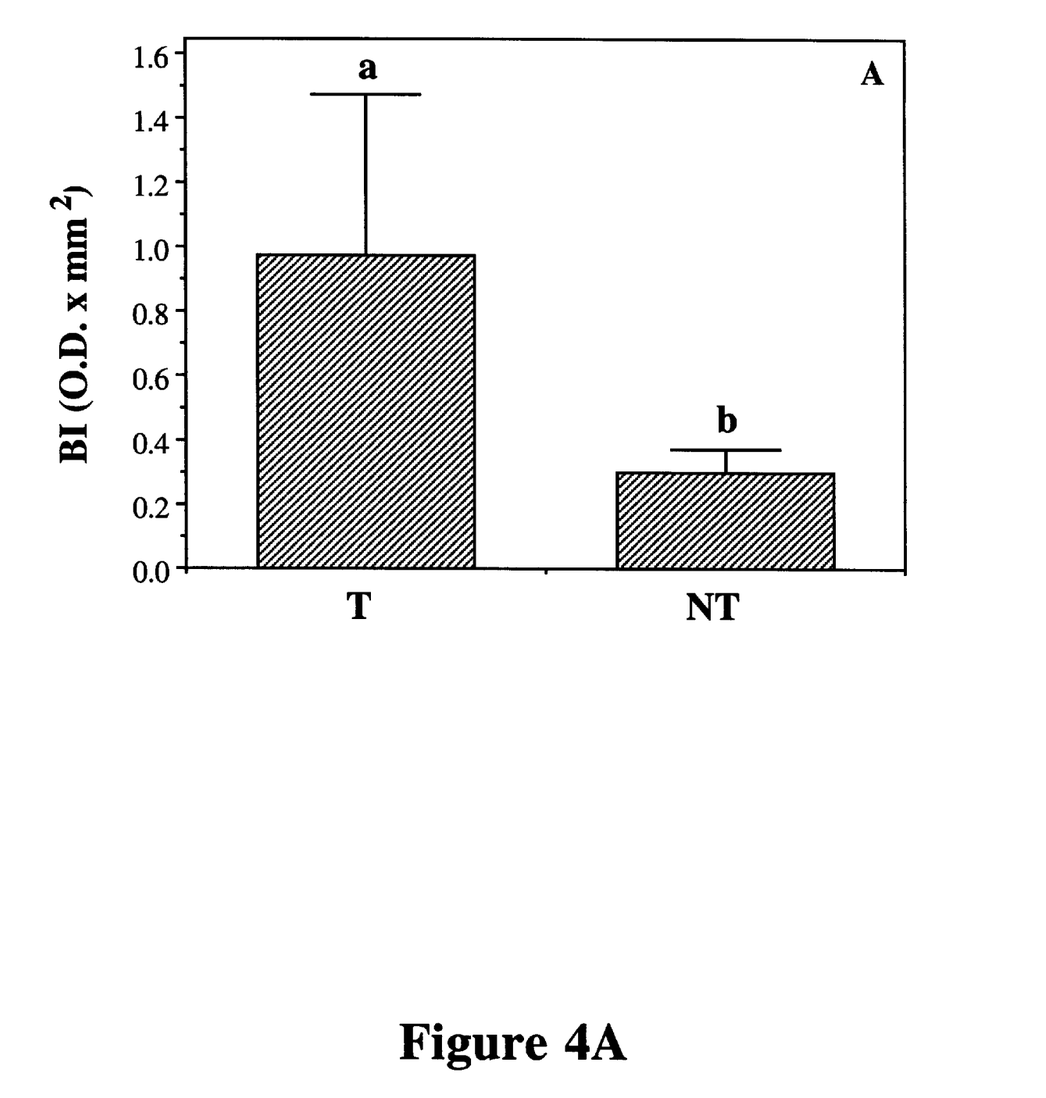
Figure 5:
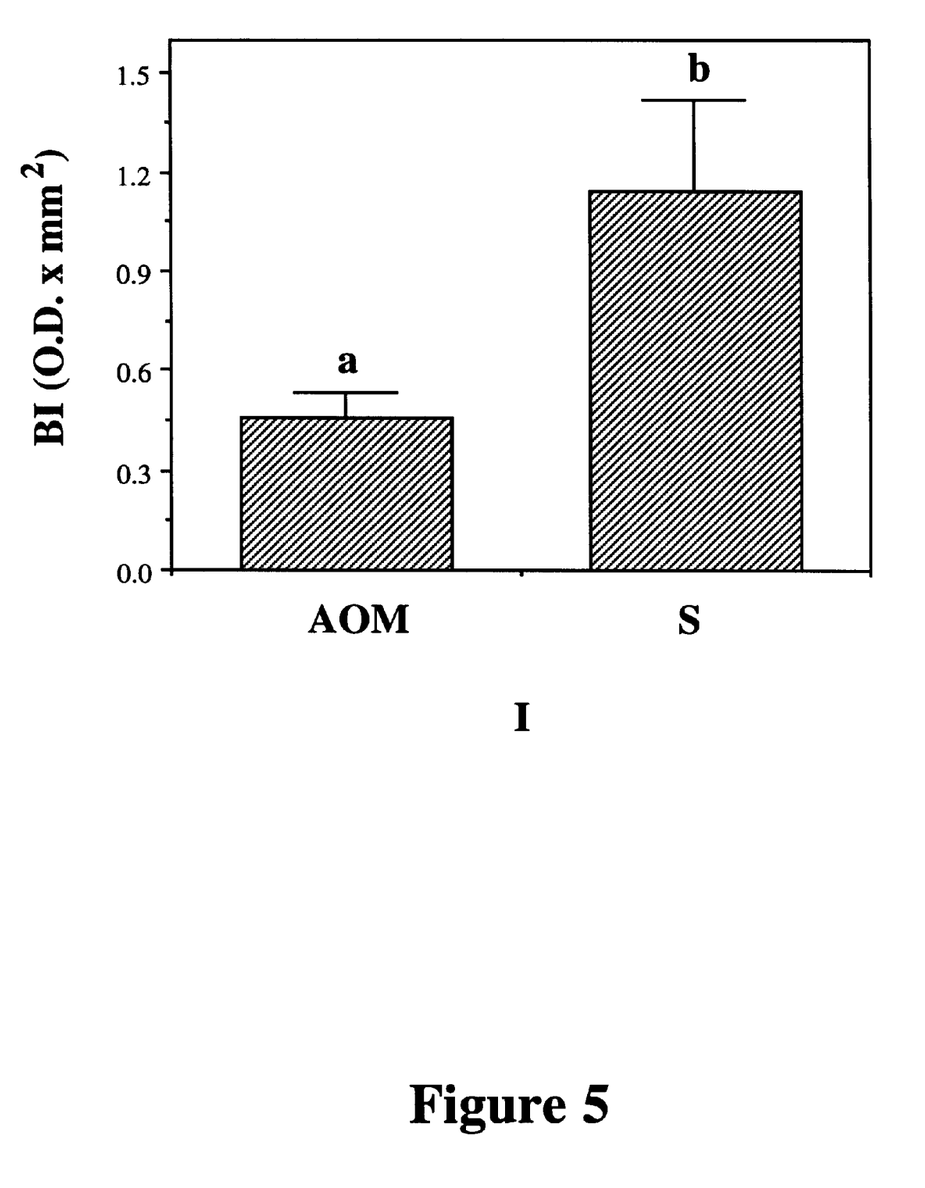
FIG. 5 shows expression of PKC ζ in fecal poly A+ RNA from rats injected with AOM or saline. See FIG. 4 legend for further details (mean±SEM: P=0.017; n=21–22).

Using the method described above, fecal poly A+ RNA from rats injected with carcinogen or saline (control) was examined for colon cancer biomarkers. We determined that protein kinase C βII expression in fecal poly A+ RNA is positively correlated with colon tumor incidence (FIG. 4A), while protein kinase C ζ is negatively correlated with tumor incidence (FIG. 5).

Figure 6:
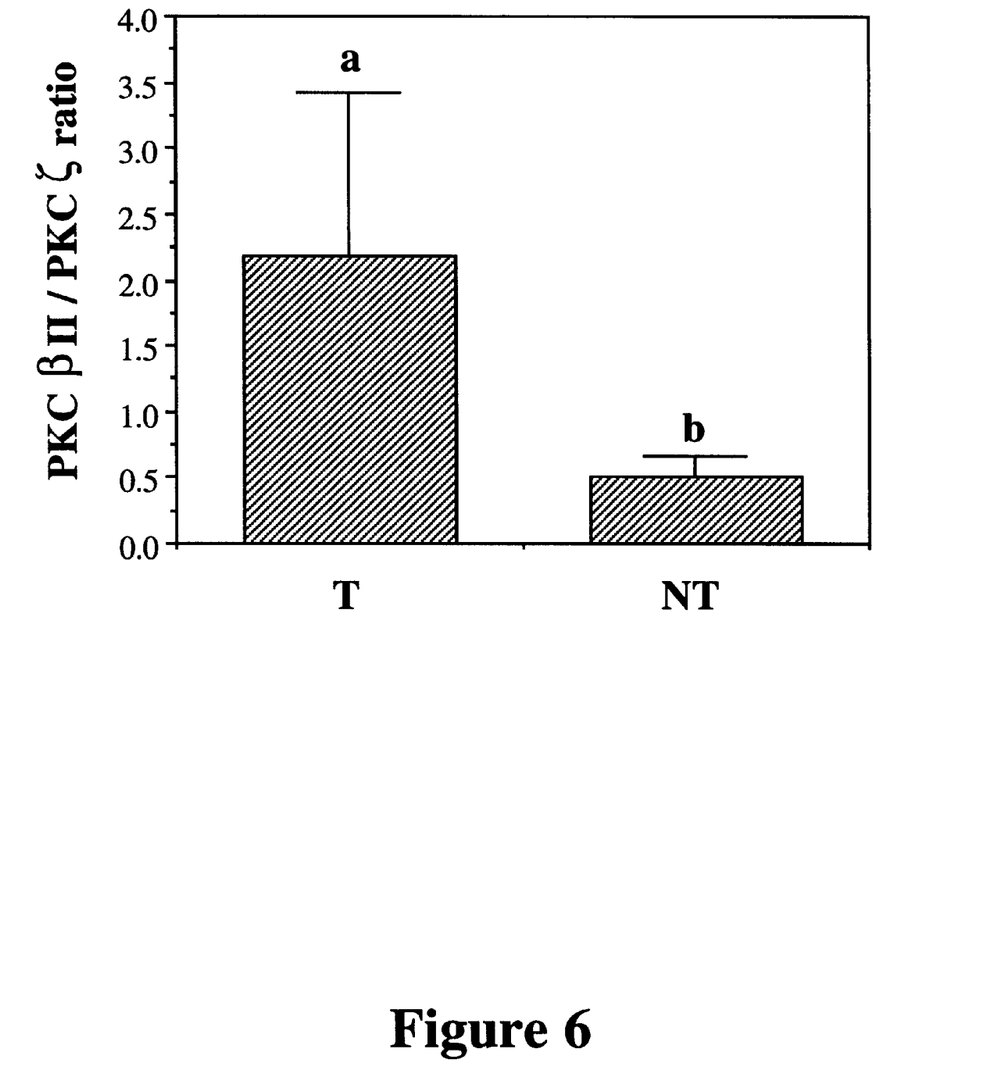
FIG. 6 shows expression of PKC βII/PKC ζ ratio in fecal poly A+ RNA from rats with or without tumors. See FIG. 4 legend for further details (mean±SEM; P=0.025; n=9–26).

The ratio of PKC βII to ζ is also strongly correlated with tumor presence (Table 1 and FIG. 6).

TABLE 1

Relationship between PKC βII: ζ ratio and tumor incidence.

| | PKC βII:ζ ratio | |
|---|---|---|
| Animals with tumors | 4.27 ± 2.37 | p = 0.02 |
| Animals without tumors | 0.71 ± 0.14 | |

EXPERIMENT 2

Utilization of Isolated Fecal Poly A+ RNA to Detect Colon Cancer Markers II

Figure 1:
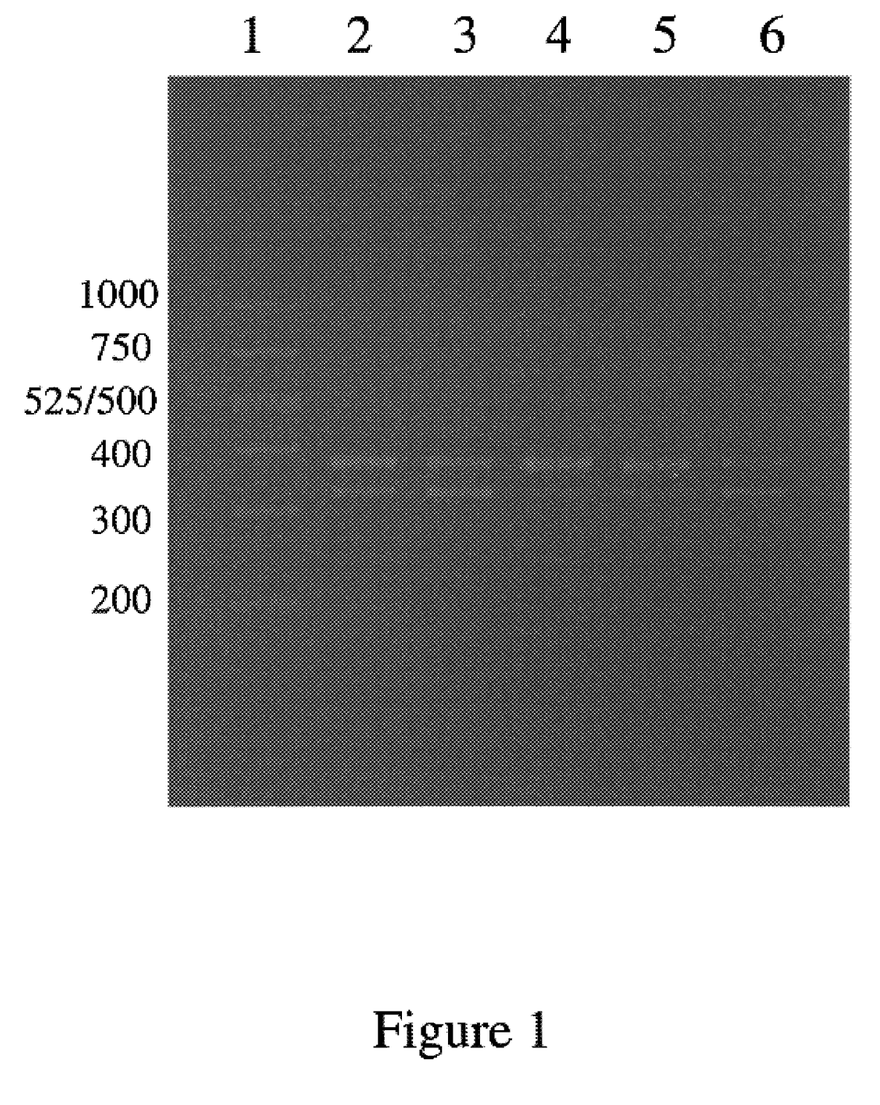
FIG. 1 shows representative competitive PCR products for determination of Liver-Fatty Acid Binding Protein (L-FABP) expression in fecal poly A+ RNA. Lane 1, marker; lane 2, rat colonic mucosa (standard); lanes 3–6, rat poly A+ RNA. Upper band is amplified sample band (390 bp); lower band is amplified internal standard (336 bp).
Figure 2:
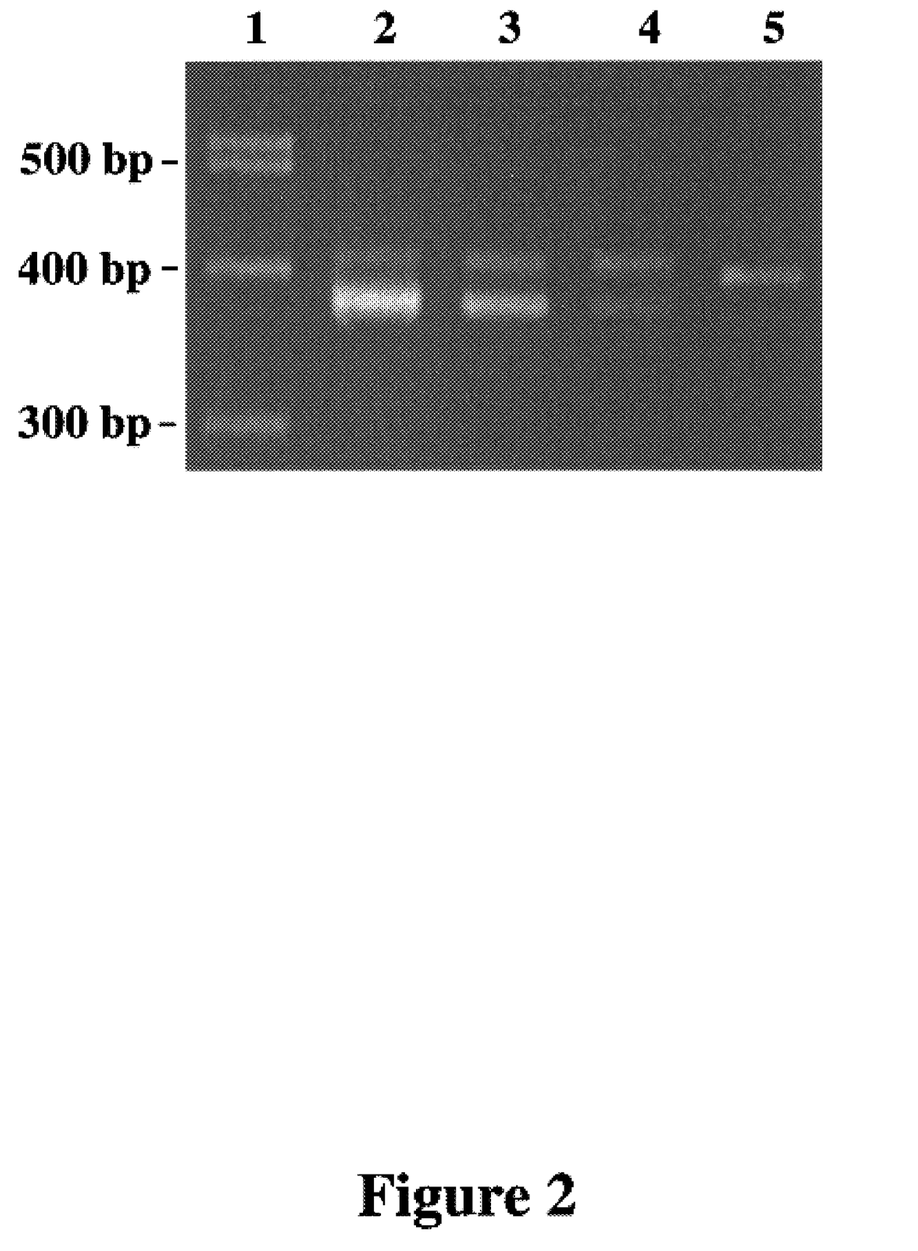
FIG. 2 shows a representative gel of RC-PCR products of PKC βII. Lane 1, marker; lanes 2–5 fecal poly A+ samples. Upper band is the amplified sample band (419 bp); the lower band is the amplified internal standard (361 bp).

Liver fatty acid binding protein (L-FABP) and intestinal fatty acid binding protein (I-FABP), expressed in colonocytes, are additional colon cancer biomarkers. Data indicates that expression of L-FABP and I-FABP are significantly depressed in carcinogen treated animals. FIG. 2 documents a typical gel containing rapid competitive PCR products for L-FABP. The upper band represents the sample (390 base pairs), whereas the lower band is the internal standard (336 base pairs).

EXPERIMENT 3

Human Clinical Trials Methodology

Clinical. Patients presenting for colonoscopy are individually typed as: 1) being free of colon cancer, 2) having adenomatous polyps (considered preneoplastic), or 3) having colon cancer (presenting histological evidence of adenocarcinomas). Thirty subjects for each group are recruited in order to reduce the effect of individual variation on the analysis. The sample size is based upon testing equality of means with a α=0.05 and detecting a difference of size α with a probability of 95% (Pearson and Hartley, 1966). To achieve this level of statistical power requires 26 individuals. Thus 30 patients protect against loss of power if a sample becomes damaged during storage or analysis. Because patients randomly present for treatment, and the disease state will not be a controlled factor, we assume the data will be randomly distributed among the potential population. Because patients with cancer are the limiting factor in sample collection, the first 30 individuals with cancer are those selected for inclusion in the study. In order to adjust for variation related to patient age, individuals free of colon cancer and those with polyps are age-matched to patients with colon cancer. Further, patients with polyps or free of pathology are selected after a sample is collected from a cancer patient.

A patient will follow a bowel preparation schedule prior to colonoscopy. Patients will receive the Golytely™ (3–4 L, Braintree Labs, Braintree, Mass.) colonoscopic preparation. This preparation was selected because it preserves surface epithelial and goblet cells and has minimal effects on a variety of colon cancer risk biomarkers. At the time of colonoscopy, the rectal vault eluate (5–50 ml) will be suctioned through the scope into a disposable suction trap. The trap will be removed and its contents transferred immediately into Lysis solution (from poly A+ Pure Kit, Ambion, Austin, Tex.) and placed on ice until the end of the case (<45 min). Samples will subsequently be stored at −80° C. until transported to the analysis lab for further processing.

Laboratory

Samples are stored at −80° C. until being thawed on ice, and the homogenate transferred to sterile tubes and the volume measured. Dilution buffer (Ambion Poly A+ Pure Kit) is added and the contents mixed by inversion and then centrifuged at 4,000×g for 15 min at 4° C. Oligo dT resin is added to the sample and the supernatant is then mixed by inversion to resuspend the oligo dT resin prior to rocking the tube on a horizontal shaker. Following centrifugation, the resin pellet is resuspended with binding buffer (Ambion Kit). The resin is then pelleted, supernatant discarded and resulting poly A+ RNA eluted from the resin and used to determine biomarker prevalence (Davidson et al., 1995). The biomarkers chosen for analysis are PKC βII and PKC ζ, based on our previous research indicating the βII isoform is positively correlated with colon tumor incidence (FIG. 4A), and the ζ isoform is negatively correlated with tumor incidence. In addition, cyclin $D_1$ (Arber, 1996), survivin (Lacasse, 1998), cyclooxygenase type II (Kutchera, 1996), p53 (El-Mahdani, 1997), and human telomerase reverse transcriptase (hTERT) (Sumida, 1999) were selected based on the cited research indicating a strong correlation between mRNA expression and tumor incidence. RC-PCR (Jiang et al., 1996) is used to detect the level of expression for each of the biomarkers.

Figure 7:
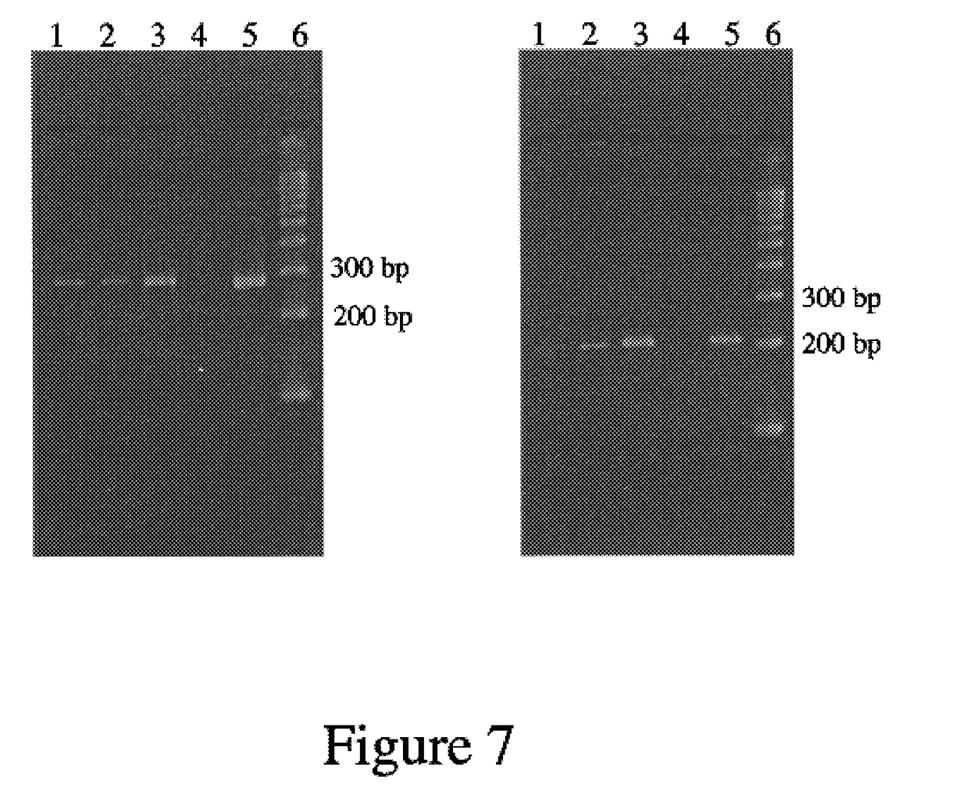
FIG. 7 shows a representative agarose gel of PKC βII (A) and PKC ζ (B) RT-PCR products from human rectal vault eluate obtained at the initiation of colonoscopy and from freshly isolated human fecal poly A+ RNA. Lanes 1 and 2, amplification from rectal vault eluate poly A+ RNA; lane 3, amplification from fecal poly A+ RNA; lane 4, minus RT negative control; lane 5, amplification from human brain poly A+ RNA (positive control); lane 6, base pair marker. PKC βII product is 280 bp, PKC ζ product is 216 bp.

A representative agarose gel showing quantitative RT-PCR of human PKC βII and ζ is shown in FIG. 7. The fidelity of all PCR reactions was confirmed by DNA sequencing (Davidson, 1994). Negative controls processed without RT yielded no detectable amplified products indicating the absence of DNA contamination. Comparable results were obtained from freshly isolated fecal samples (refer to FIG. 7 for details).

Data is analyzed using the GLM models of SAS. Differences between groups are determined by orthogonal contrasts. Data from healthy individuals are compared with those having either polyps or cancer to determine if the presence of the pathologies affect the relative mRNA expression for the genes with biomarker potential. In addition, a contrast of the individuals with polyps vs those with cancer is performed to determine if the expression changes with stage of the tumorigenic process.

EXPERIMENT 4

Detection of Fecal Protein Kinase C βII AND ζMessenger RNA Colon Cancer Biomarkers The animal use protocol conformed to NIH guidelines and was approved by the University Animal Care Committee of Texas A&M University. Forty-eight male weanling Sprague-Dawley rats (Harlan Sprague-Dawley, Houston, Tex.) were randomly divided into two groups as previously described (Chang et al., 1997) and given two types of injection (carcinogen or saline). Animals were housed individually in suspended cages in a temperature and humidity controlled animal facility with a 12 h light/dark cycle. Food and distilled water were freely available. Forty-eight h food intakes and fecal outputs were measured during the study. Body weights were recorded weekly.

Carcinogen Administration and Fecal Collection

After a 2 week acclimation period, rats were given two s.c. injection of AOM (Sigma Chemical Co., St. Louis, Mo.) at a dose of 15 mg/kg body weight or an equal volume of saline (one injection/week) (Chang et al., 1997). Animals were killed by $CO_2$ asphyxiation 36 weeks after the second injection. The colon was subsequently removed and the most distal fecal pellet collected. The pellet was immediately placed in Lysis solution for RNA isolation (Ambion Totally RNA kit, Austin, Tex.). The colon was then visually inspected for tumors and tumor typing was determined (Chang et al., 1997). Briefly, tissue sections were fixed in 4% buffered formalin, embedded in paraffin, and stained with eosin and hematoxylin. Slides were then microscopically evaluated for tumors as previously described (Chang et al., 1997). Following removal of suspected tumors for histological evaluation, the remaining colonic sections were gently scraped with a microscopic slide and the mucosa used for determination of steady-state levels of PKC isozyme mRNA. Histological evaluation of this method indicated that epithelial cells and lamina propria down to the muscularis mucosa were removed (Lee et al., 1992).

RNA Isolation

Fecal poly A+ RNA was prepared as described above. Quantification of fecal poly A+ RNA was performed as previously described (Davidson et al., 1995). Briefly, samples were quantitated by blotting fecal poly A+ RNA onto a positively charged nylon membrane (Roche, Indianapolis, Ind.). A biotinylated oligo (dT) probe (Promega, Madison, Wis.) was hybridized to the poly A+RNA followed by detection with streptavidin-alkaline phosphatase. Dilutions of colonic musocal total RNA of known concentration (as determined from absorbance at 260 nm) were also blotted to generate a standard curve. For concentration calculations, it was assumed that poly A+ RNA constitutes 3% of total RNA.

Reverse Transcription-Polymerase Chain Reaction (RT-PCR) Assay for Negative Controls (PKC γ and PKC βI)

Aliquots of 40 ng fecal poly A+ RNA in a 50 μl reaction were reverse transcribed to generate first strand cDNA using Superscript II reverse transcriptase (Gibco-BRL, Gaithersburg, Md.) as previously described (Davidson et al., 1995). PCR was performed using Expand High Fidelity DNA polymerase (Roche, Indianapolis, Ind.). The 50 μl PCR reaction consisted of 1× PCR buffer, 2% DMSO, 0.05 mM dNTPs, 1.5 mM $MgCl_2$, 20 pmol each of forward and reverse primer, 2.6U Expand High Fidelity DNA polymerase and 10 μl of RT reaction. Rat brain cDNA was run as a positive control. PCR was performed using a Perkin-Elmer 2400 thermal cycler (Perkin-Elmer, Foster City, Calif.) with the following amplification program: 15 s denaturation (94°), 15 s annealing (59° C.) and 45 s extension (74° C.) for 40 cycles. PCR products were analyzed on a 4% agarose gel followed by ethidium bromide staining. All PCR products were sequenced to ensure the fidelity of amplification (Davidson et al., 1994). The primer pair for PKC γ was as follows (347 bp); forward, 5'-TTGATGGGGAAGATGAGGAGG-3', Sequence ID No. 1; reverse, 5'-GAAATCAGCTTGGTCGATGCTG-3', Sequence ID No. 2. The primer pair for PKC βI was as follows (639 bp): forward, 5'-TGTGAT-GGAGTATGTGAACGGGGG-3', Sequence ID No. 3; reverse, 5'-TCGAAGTTGGAGGTGTCTCGCTTG-3', Sequence ID No. 4.

Figure 3:
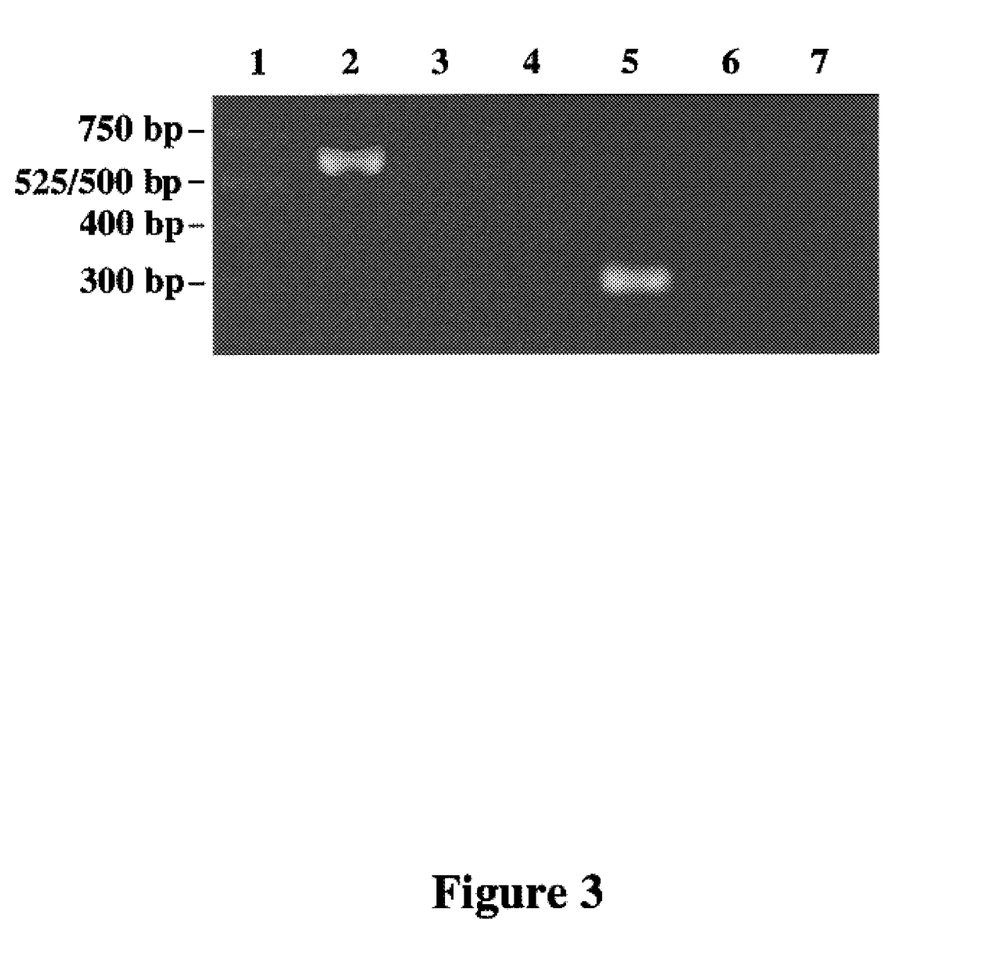
FIG. 3 shows a representative gel of RT-PCR products of PKC βI and PKCγ in brain but not in fecal poly A+ RNA. Lane 1, marker; lane 2, PKC βI in brain (639 bp); lanes 3 and 4, PKC βI in fecal poly A+ RNA; lane 5, PKC γ in brain (347 bp); lanes 6 and 7, PKC γ in fecal poly A+ RNA.

Rapid Competitive Reverse Transcription-Polymerase Chain Reaction Assay For Fecal and Mucosal PKC ζ and βII Rapid competitive RT-PCR was performed in order to semi-quantitatively determine the PKC ζ and βII fecal and mucosal mRNA levels as previously described (Jiang et al., 1996). Using this method, relative gene expression was determined by co-amplifying an exogenous DNA target ('internal standard') with a different size than the sample cDNA but with identical 5' and 3' ends. This allows for competition between the sample cDNA and the internal standards for primers (Jiang et al., 1996). Internal standards were prepared as described previously (Davidson et al., 1995). Fecal poly A+ RNA was processed as described above. In addition, 6 µg of mucosal total RNA was reverse transcribed in a 50 µl reaction and 10 µl was amplified in the presence of either 140 fg of PKC ζ internal standard or 31.2 fg PKC βII internal standard. The primer pair for the PKC ζ internal standard was (561 bp): forward, 5'-CGATGGGGTGGATGGGATCAAAA-3', Sequence ID No. 5; reverse, 5'-GTATTCATGTCAGGGTTGTCTGGA-TTTCGGGGGCG-3', Sequence ID No. 6, and for PKC ζ was (680 bp): forward, 5'-CGATGGGG-TGGATGGGATCAAAA-3', Sequence ID No. 7; reverse, 5'-GTATTCATGTCAGGGTTGTCTG-3', Sequence ID No. 8. The primer pair for PKC βII internal standard was (361 bp): forward, 5'-TATCTGGGATGGGGTGACAACCGA-GATCATTGCTTA-3', Sequence ID No. 9; reverse, 5'-CGGTCGAAGTTTTCAGCGTTTC-3', Sequence ID No. 10. The primer pair for PKC βII was (419 bp): forward, 5'-TATCTGGGATGGGGTGACAACC-3', Sequence ID No. 11; reverse, 5'-CGGTCGAAGTTTTCAGCGTTTC-3', Sequence ID NO. 12. PCR products were separated on a 4% agarose gel and stained with ethidium bromide. A representative gel is shown in FIG. 3. Gels were scanned and band intensities quantitated with BioImage software version 2.1 (Ann Arbor, Mich.). The relative amount of sample mRNA was calculated by dividing the sample band intensity by the internal standard band intensity. Specific amplification of mRNA was monitored by running PCR negative controls consisting of tubes containing either sample RNA without reverse transcription, reverse transcribed sample without mimic, or mimic only. To ensure reproducibility of results, selected samples were amplified in duplicate. In addition, the fidelity of all PCR reactions was confirmed by DNA sequencing (Jiang et al., 1996).

Statistical Analysis

Data were analyzed to determine the effects of carcinogen and presence of tumor using one-way ANOVA. When P-values were <0.05 for the effects of tumor or carcinogen, total means were separated using Duncan's multiple range test.

RESULTS

Colon Carcinoma Incidence

There was no evidence of carcinoma in any saline injected animal, whereas 64% of carcinogen injected rats had carcinomas at the time of death.

Effect of Carcinogen and Presence of Tumor on Fecal and Mucosal PKC Isozyme mRNA Levels To determine the specificity of this non-invasive procedure, PKC βI and γ primers were used as negative controls (Davidson et al., 1994; Davidson et al., 1995). No amplified products were detected after 40 cycles in any fecal poly A+ or scraped colonic mucosa total RNA samples (FIG. 3, lanes 3, 4, 6 and 7). However, both isozymes were detected using brain total RNA (positive control, lanes 2 and 5).

Figure 4B:
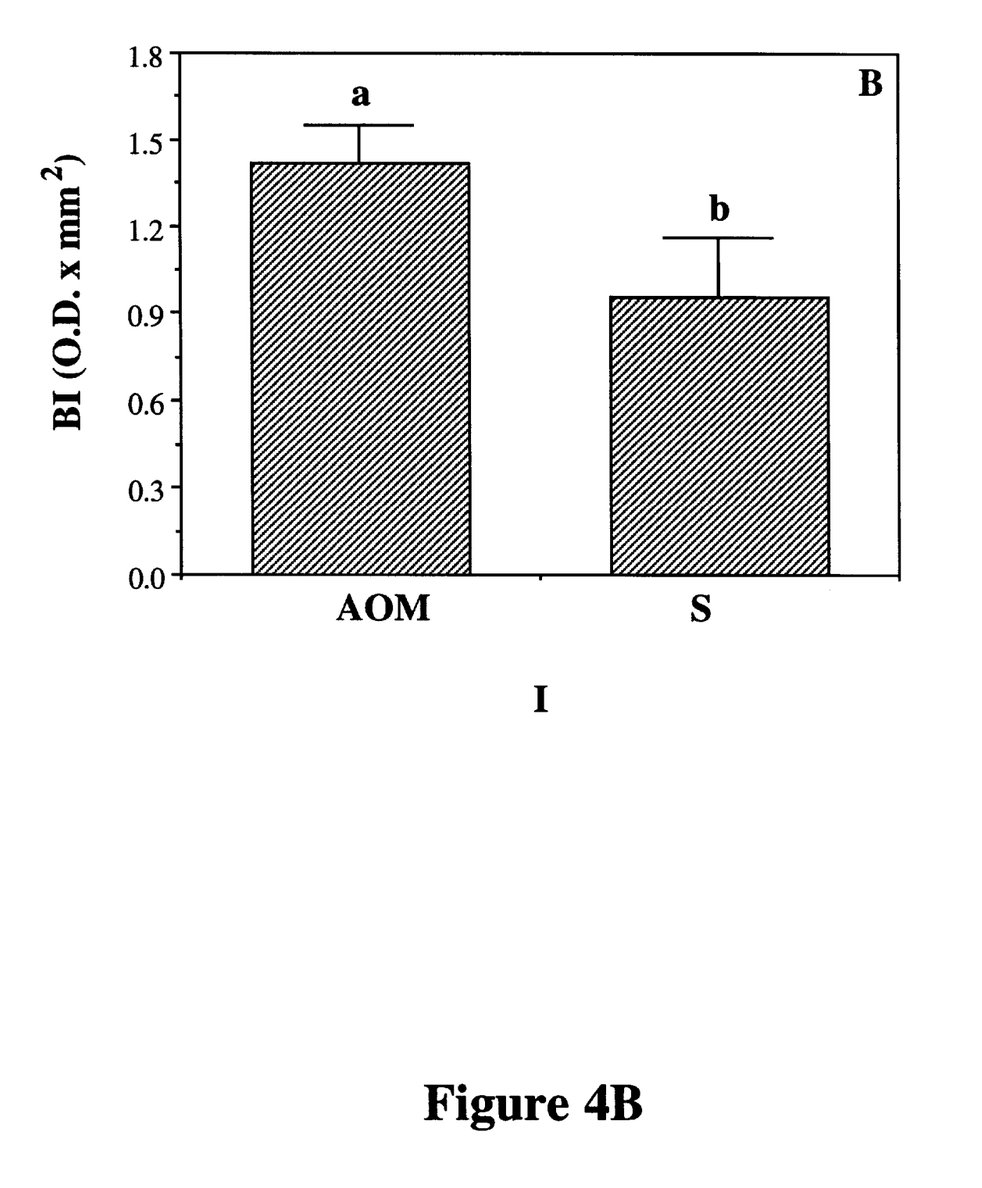

PCR products for PKC βII were detected in all fecal and mucosal samples. Samples processed without reverse transcriptase were used as negative controls and yielded no detectable amplified products (data not shown). Using semi-quantitative mimic PCR, it was determined that fecal PKC βII mRNA levels were altered by the presence of a tumor with tumor-bearing animals having 3-fold higher (P<0.05) PKC βII expression as compared with animals without tumors, as seen in FIG. 4A. In contrast, there was no effect of tumor incidence on mucosal PKC βII expression. However, there was a significant effect (P<0.05) of injection on mucosal PKC βII expression. Specifically, carcinogen (AOM) injection increased mucosal PKC βII mRNA expression compared with saline controls (FIG. 4B).

Colonic mucosal PKC ζ expression in rats injected with AOM was less than half (P<0.05) that of saline control, as shown in FIG. 5. Since tumor incidence exerts a reciprocal effect on fecal PKC β and PKC βII expression, data were also expressed as the ratio between PKC βII and PKC ζ. The isozyme ratio was strongly related to tumor incidence, i.e. ratio for animals with tumors was 2.18±1.25 (n=9), animals without tumors was 0.50±0.6 (n=26), P=0.025 (FIG. 6). These data demonstrate that PKC βII and PKC ζ may serve as non-invasive markers for development of colon tumors.

EXPERIMENT 5

Enhancement of Noninvasive mRNA-Gene Expression Profiling Using Biochip Technology mRNA isolated from feces can be utilized in combination with complimentary DNA (cDNA) and oligonucleotide microarray technology in order to noninvasively determine complex patterns of gene expression, and mutations (Bowtell, 1999; Duggan, 1999; Lipshutz, 1999). Biochip technology is described in many publications (including Bowtell, 1999; Duggan, 1999; Lipshutz, 1999 which are incorporated herein by reference), and is known in the art. This technology allows for large-scale, high-throughput monitoring of gene expression patterns of up to 40,000 genes (Bowtell, 1999; Duggan, 1999; Lipshutz, 1999). Generated data provide insight into the extent of expression differences underlying colonic disease, e.g., malignancy, and reveal genes that may prove useful as diagnostic or prognostic markers.

Description of the Method 0.1–1 µg of fecal poly A+ RNA isolated from animal/human subjects as previously described, is processed in strict accordance to the following protocols or others known in the art. For example, following fecal mRNA isolation, cDNA synthesis will be performed using select primers, such as, for example (a T7-(dT)$_{24}$-3' primer: 5'-GGCCAGTGAATTGTAATACGACTCACTATAGGG-AGGCGG-(dT)$_{24}$-3') (Sequence ID No. 13). Subsequently, in vitro transcription is performed to generate labeled samples for hybridization. This technology is known in the art. cRNA fragmentation, target hybridization, fluidics station setup, probe array washing and staining, probe array scan, and initial data analysis are performed according to procedures known in the art. The precise composition of the probe microarray can vary depending on the specific package of genes being surveyed. The microarrays are currently capable of simultaneously quantitating mRNA levels (gene expression) for thousands of genes in a single experiment. Quantitative changes in mRNA expression patterns of approximately 2-fold or greater can be detected (Bowtell, 1999; Duggan, 1999; Lipshutz, 1999). With regard to specificity, hybridization discrimination of low abundance transcripts is currently 1:50,000–1:100,000.

Fecal (exfoliated colonic cell) mRNA isolation methodology in combination with Biochip technology can be utilized to assay for a number of gene expression applications. For example:

1. Tissue comparison: diseased (e.g., colon cancer, colitis) vs. unaffected colon, as a means of predicting disease onset.
2. Time point experiments: determine patient status over time.
3. Drug response in the body.

Explanation of GeneChip Probe Arrays

GeneChip probe arrays are known in the art and in essence are manufactured using technology that combines photolithographic methods and combinational chemistry. Tens to hundreds of thousands of different oligonucleotide probes are synthesized, for example, in a 1.28 cm×1.28 cm area on each array. Each probe type is located in a specific area on the probe array called a probe cell. Each probe cell contains millions of copies of a given probe. In use, biotin-labeled RNA fragments, referred to as the RNA targets, are hybridized to the probe array. The hybridized probe array is stained with, for example, streptavidin phycoerythrin conjugate and scanned by the Hewlett-Packard (HP) GeneArray™ Scanner at the excitation wavelength of 488 nm. The amount of light emitted at 570 nm is proportional to bound target at each location on the probe array.

Target Preparation

Double stranded cDNA is synthesized from poly A+ messenger RNA isolated from tissue or cells. An in vitro reaction is then performed to produce biotin-labeled cRNA from the cDNA. The cRNA is fragmented before hybridization.

Target Hybridization

After the biotin-labeled cRNA is fragmented, a hybridization cocktail is prepared, which includes the fragmented cRNA, probe array controls, BSA, and herring sperm DNA. A cleanup procedure is performed on the hybridization cocktail after which approximately 200 µL is applied to the probe array. It is then hybridized to the oligonucleotide probes on the probe array during a 16-hour incubation at 45° C.

Probe Array Washing and Staining

Immediately following the hybridization, the hybridized probe array undergoes a washing and staining protocol as known in the art.

Probe Array Scan

Once the probe array has been hybridized, stained, and washed, it is scanned as known in the art.

Data Analysis

Data are analyzed using the GeneChip software available in the art. The data image is analyzed for probe intensities and results are reported in tabular and graphical formats.

REFERENCES

Albaugh, G. P., Iyengar, A., Malayeri, M., Bala, S., Nair, P. P. Isolation of exfoliated colonic epithelial cells, a novel, non-invasive approach to the study of cellular markers. *Int. J. Cancer* 52:347–350, 1992.

Arber, N., Hibshoosh, H., Moss, S. F., Sutter, M. T., Zhang, Y., Begg, M., Wang, S., Weinstein, I. B. and Holt, P. R. Increased expression of cyclin D1 is an early event in multistage colorectal carcinogenesis. *Gastroenterology* 110:669–674, 1996.

Baum, C. L., Wali, R. K., Sitrin, M. D., Bolt, G. J. G., Brasitus, T. A. 1–2, dimethylhydrazine-induced alterations in protein kinase C activity in the rat prenoplastic colon. *Cancer Research* 50:3915–3920, 1990.

Blobe, G. C., Stribling, S., Obeid, L. M. and Hannun, Y. A. Protein kinase C isoenzymes: Regulation and function. *Cancer Surveys: Cell Signalling* 27:213–248, 1996.

Bowtell, D. D. Options available-from start to finish-for obtaining expression data by microarray. *Nature Genetics Suppl.* 21:25–32, 1999.

Caldas, C., Hahn, S. A., Hruban, R. H., Redston, M. S., Yeo, C. J. and Kern, S. E. Detection of K-ras mutations in the stool of patients with pancreatic adenocarcinoma and pancreatic ductal hyperplasia. *Cancer Research* 54:3568–3573, 1994.

Chang, W.-C. L., Chapkin, R. S. and Lupton, J. R. Predictive value of proliferation, differentiation and apoptosis as intermediate markers for colon tumorigenesis. *Carcinogenesis* 18:721–730, 1997.

Chapkin, R. S., Gao, J., Lee, D. Y. K. and Lupton, J. R. Effect of fibers and fats on rat colon protein kinase C activity: correlation to cell proliferation. *J. Nutr.* 123:649–655, 1993.

Chapkin, R. S., Clark, A. E., Davidson, L. A., Schroeder, F., Zoran, D. L. and Lupton, J. R. Dietary fiber differentially alters cellular fatty acid-binding protein expression in exfoliated colonocytes during tumor development. *Nutrition and Cancer* 32:107–112, 1998.

Craven, P. A., DeRubertis, F. R. Alterations in protein kinase C in 1,2-dimethylhydrazine induced colonic carcinogenesis. *Cancer Research* 52:2216–2221, 1992.

Davidson, L. A., Jiang, Y.-H., Derr, J. N., Aukema, H. M., Lupton, J. R. and Chapkin, R. S. Protein kinase C isoforms in human and rat colonic mucosa. *Archives of Biochemistry and Biophysics* 312:547–553, 1994.

Davidson, L. A., Lupton, J. R., Jiang, Y.-H., Chang, W. C., Aukema, H. M. and Chapkin, R. S. Dietary fat and fiber alter rat colonic protein kinase C isozyme expression. *Journal of Nutrition* 125:49–56, 1995b.

Davidson, L. A., Jiang, Y. H., Lupton, J. R. and Chapkin, R. S. Noninvasive detection of putative biomarkers for colon cancer using fecal messenger RNA. *Cancer Epidemiol. Biomarkers & Prev.* 4:643–647, 1995.

Davidson, L. A., Aymond, C. M., Jiang, Y. H., Turner, N. D., Lupton, J. R. and Chapkin, R. S. Noninvasive detection of fecal protein kinase C βII and ζ messenger RNA: putative biomarkers for colon cancer. *Carcinogenesis* 19:253–257, 1998.

Duggan, D. J., Bittner, M., Chen, Y., Meltzer, P. and Trent, J. M. Expression profiling using cDNA microarrays. *Nature Genetics Suppl.* 21:10–14, 1999.

El-Mahdani, N., Vaillant, J. C., Guiguet, M., Prevot, S., Bertrand, C., Parc, R., Bereziat, G., and Hermelin, B. Overexpression of p53 mRNA in colorectal cancer and its relationship to p53 gene mutation. *Br. J. Cancer* 75:528–536, 1997.

Fearon, E. R. Human cancer syndrome: Clues to the origin and nature of cancer. *Science* 278:1043–1050, 1997.

Hibi, K., Robinson, R., Booker, S., Wu, L., Hamilton, S. R. Molecular detection of genetic alterations in the serum of colorectal cancer patients. *Cancer Res.* 58:1405–1407, 1998.

Iyengar, V., Albaugh, G. P., Lohani, A. and Nair, P. O. Human stools as a source of viable colonic epithelial cells. *FASEB Journal* 5:2856–2859, 1991.

Jiang, Y. H., Davidson, L. A., Lupton, J. R., and Chapkin, R. S. Rapid competitive PCR determination of relative gene expression in limiting tissue samples. *Clin. Chem.* 42:227–231, 1996.

Jiang, Y. H., Lupton, J. R. and Chapkin, R. S. Dietary fish oil blocks carcinogen-induced down-regulation of colonic protein kinase C isozymes. *Carcinogenesis* 18:351–357, 1997.

Kopp, R., Noelke, B., Sauter, G., Schildberg, F. W., Paumgartner, G., Pfeiffer, A. Altered protein kinase C activity in biopsies of human colonic adenomas and carcinomas. *Cancer Res.* 51:205–210, 1991.

Kuranami, M., Powell, C. T., Hug, H., Zeng, Z., Cohen A., Guillem, J. G. Differential expression of protein kinase C isoforms in human colorectal cancers. *J. Surgical Research* 58:233–239, 1995.

Kutchera, W., Jones, D. A., Matsunami, N., Groden, J., McIntyre, T. M., Zimmerman, G. A., White, R. L. and Prescott, S. M. Prostaglandin H synthase 2 is expressed abnormally in human colon cancer: evidence for a transcriptional effect. *Proc. Natl. Acad. Sci.* 93:4816–4820, 1996.

LaCasse, E. C., Baird, S., Komeluk, R. G. and MacKenzie, A. E. The inhibitors of apoptosis (LAPs) and their emerging role in cancer. *Oncogene* 17:3247–3259, 1998.

Lahm, H., Hoeflich, A., Rieger, N., Wanke, R. and Wolf, E. Identification of transgenic mice by direct PCR analysis of lysates of epithelial cells obtained from the inner surface of the rectum. *Transgenic Res.* 7:131–134, 1998.

Lee, D. Y., Lupton, J., Chapkin, R. S. Prostaglandin profile and synthetic capacity of the colon: comparison of tissue sources and subcellular fractions. *Prostaglandins* 43:143–164, 1992.

Levin, B. and Bond, J. H. Colorectal cancer screening: Recommendation of the U.S. preventive services task force. *Gastroenterology* 111:1381–1384, 1996.

Lipshutz, R. J., Fodor, S. P., Gineras, T. R. and Lockhart, D. J. High density synthetic oligonucleotide arrays. *Nature Genetics Microarray Supplement* 21:20–24, 1999.

Mandel, J. S. Colorectal cancer screening. *Cancer and Metastasis Rev.* 16:263–279, 1997.

McLeod, H. L. and Murray, G. I. Tumor markers of prognosis in colorectal cancer. *Br. J. Cancer* 79:191–203, 1999.

Nollau, P., Moser, C., Weinland, G. and Wagener, C. Detection of K-ras mutations in stools of patients with colorectal cancer by mutant-enriched PCR. *Int. J. Cancer* 66:332–336, 1996.

Potten, C. S., Schofield, R., Lajtha, L. G. A comparison of cell replacement in bone marrow, testis and three regions of epithelium. *Biochim. Biophys Acta* 560:281–299, 1979.

Roy, H. K., Bissonnette, M., Frawley, B. P., Wali, R. K., Niedziela, S. M., Earnest, D., Brasitus, T. A. Selective preservation of protein kinase C-ζ in the chemoprevention of azoxymethane-induced colonic tumors by piroxicam. *FEBS Letters* 366:143–145, 1995.

Sakanoue Y., Hatada, T., Kusunoki, M., Yanagi, H., Yamamura, T., Utsunomiya, J. Protein kinase C activity as marker for colorectal cancer. *Int. J Cancer* 48:803–806, 1991.

Sidransky, D., Tokino, T., Hamilton, S. R., Kinzler, K. W., Levin, B., Frost, P. and Vogelstein, B. Identification of ras-oncogene mutations in the stool of patients with curable colorectal tumors. *Science* 256:3102–3105, 1992.

Sidransky, D. Molecular markers in cancer: can we make better predictions? *International Journal of Cancer* 64:1–2, 1995.

Silverberg, E. and Lubera, J. Cancer Statistics. *CA Cancer J. Clin* 38:16–17, 1988.

Sumida, T., Hamakawa, H., Sogawa, K., Sugita, A., Tanioka, H. and Ueda, N. Telomerase components as a diagnostic tool in human oral lesions. *Int. J. Cancer* 80:1–4, 1999.

Tobi, M., Luo, F.-C. and Ronai, Z. Detection of K-ras mutation in colonic effluent samples from patients without evidence of colorectal carcinoma. *Journal of the National Cancer Institute* 86:1007–1010, 1994.

Wali, R. K., Frawley, B. P., Hartmann, S., Roy, H. K., Khare, S., Scaglione-Sewell, B. A., Earnest, D. L., Sitrin, M. D., Brasitus, T. A., Bissonnette, M. Mechanism of action of chemoprotective ursodeoxycholate in the azoxymethane model of rat colonic carcinogenesis: potential roles of protein kinase C-α, βII, and -ζ. *Cancer Res.* 55:5257–5264, 1995.

WFR/AICR. In Food, Nutrition and Prevention of Cancer: a global perspective. pp. 18–72. *American Institute for Cancer Research*, Washington, D.C., 1997.

One skilled in the art readily appreciates that the present invention is well adapted to carry out the objectives and obtain the ends and advantages mentioned as well as those inherent therein. Systems, biochemical compositions, treatments, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

What is claimed is:

1. A method for non-invasively determining the expression of PKC isozymes in colonocytes of a patient comprising:
   directly isolating from said patient polyA+RNA from feces, containing sloughed colonocytes; and
   assaying the isolated polyA+RNA and determining the level, in the isolated A+RNA, of mRNA encoding PKC isozymes wherein the PKC isozyme are PKC ζ and PKC βII.

2. The method of claim 1, wherein the ratio of expression of PKC βII to PKC ζ is determined.

3. The method of claim 2, further comprising the step of comparing the ratio of expression of PKC βII to PKC ζ in said patient with similarly determined ratios of PKC βII to PKC ζ in other patients with known conditions.

4. The method of claim 3, wherein the level of expression of PKC βII to PKC ζ in said patient is compared with similarly determined ratios of PKC βII to PKC ζ in at least two other patients, one with colon cancer and one without colon cancer.

5. The method of claim 2, wherein the level of PKC ζ is determined using the primer pair having Sequence ID Numbers 7 and 8, and the level of PKC βII is determined using the primer pair selected from the group consisting of the primers having Sequence ID Numbers 11, and 12.

6. A method for non-invasively detecting colonic biomarkers in a patient using fecal messenger RNA comprising:
   directly isolating, from said patient, polyA+RNA from feces containing sloughed colonocytes; and
   assaying the isolated polyA+RNA and determining the level, in the isolated polyA+RNA, of mRNA encoding colonic biomarkers wherein the colonic biomarker are PKC ζ and PKC βII.

7. The method of claim 6, wherein the ratio of expression of PKC βII to PKC ζ is determined.

8. The method of claim 7, further comprising the step of comparing the ratio of expression of PKC βII to PKC ζ in said patient with similarly determined ratios of PKC βII to PKC ζ in at least two other patients, one with colon cancer and one without colon cancer.

9. The method of claim 6, wherein the level of PKC ζ is determined using at least one primer selected from the group consisting of the primers having Sequence ID Numbers 5, 6, 7, and 8, and the level of PKC βII is determined using at least one primer selected from the group consisting of the primers having Sequence ID Numbers 9, 10, 11, and 12.

10. A method for non-invasively screening for colon cancer in a patient comprising:
    detecting the expression of PKC ζ and PKC βII in sloughed colonocytes in said patient's feces; and
    correlating the expression of PKC ζ and PKC βII with the presence or absence of colon cancer in said patient.

11. The method of claim 10, wherein the ratio of expression of PKC βII to PKC ζ is determined.

12. The method of claim 10, further comprising the step of comparing the ratio of expression of PKC βII to PKC ζ in said patient with similarly determined ratios of PKC βII to PKC ζ in at least two other patients, one with colon cancer and one without colon cancer.

13. The method of claim 10, wherein the level of PKC ζ is determined using at least one primer selected from the group consisting of the primers having Sequence ID Numbers 5, 6, 7, and 8, and the level of PKC βII is determined using at least one primer selected from the group consisting of the primers having Sequence ID Numbers 9, 10, 11, and 12.

* * * * *

SEQUENCE LISTING

<160> NUMBER OF SEQ ID NOS: 12

<210> SEQ ID NO: 1
<211> LENGTH: 21
<212> TYPE: DNA
<213> ORGANISM: Rattus sp.

<400> SEQUENCE: 1
ttgatgggga agatgaggag g                                    21

<210> SEQ ID NO: 2
<211> LENGTH: 22
<212> TYPE: DNA
<213> ORGANISM: Rattus sp.

<400> SEQUENCE: 2
gaaatcagct tggtcgatgc tg                                   22

<210> SEQ ID NO: 3
<211> LENGTH: 24
<212> TYPE: DNA

-continued

<213> ORGANISM: Rattus sp.

<400> SEQUENCE: 3
tgtgatggag tatgtgaacg gggg                                    24

<210> SEQ ID NO: 4
<211> LENGTH: 24
<212> TYPE: DNA
<213> ORGANISM: Rattus sp.

<400> SEQUENCE: 4
tcgaagttgg aggtgtctcg cttg                                    24

<210> SEQ ID NO: 5
<211> LENGTH: 23
<212> TYPE: DNA
<213> ORGANISM: Rattus sp.

<400> SEQUENCE: 5
cgatggggtg gatgggatca aaa                                     23

<210> SEQ ID NO: 6
<211> LENGTH: 35
<212> TYPE: DNA
<213> ORGANISM: Rattus sp.

<400> SEQUENCE: 6
gtattcatgt cagggttgtc tggatttcgg gggcg                         35

<210> SEQ ID NO: 7
<211> LENGTH: 23
<212> TYPE: DNA
<213> ORGANISM: Rattus sp.

<400> SEQUENCE: 7
cgatggggtg gatgggatca aaa                                     23

<210> SEQ ID NO: 8
<211> LENGTH: 22
<212> TYPE: DNA
<213> ORGANISM: Rattus sp.

<400> SEQUENCE: 8
gtattcatgt cagggttgtc tg                                      22

<210> SEQ ID NO: 9
<211> LENGTH: 36
<212> TYPE: DNA
<213> ORGANISM: Rattus sp.

<400> SEQUENCE: 9
tatctgggat ggggtgacaa ccgagatcat tgctta                        36

<210> SEQ ID NO: 10
<211> LENGTH: 22
<212> TYPE: DNA
<213> ORGANISM: Rattus sp.

<400> SEQUENCE: 10
cggtcgaagt tttcagcgtt tc                                      22

<210> SEQ ID NO: 11
<211> LENGTH: 22

-continued

```
<212> TYPE: DNA
<213> ORGANISM: Rattus sp.

<400> SEQUENCE: 11
tatctgggat ggggtgacaa cc                                              22

<210> SEQ ID NO: 12
<211> LENGTH: 22
<212> TYPE: DNA
<213> ORGANISM: Rattus sp.

<400> SEQUENCE: 12
cggtcgaagt tttcagcgtt tc                                              22
```